(12) United States Patent
Takamatsu et al.

(10) Patent No.: US 11,234,656 B2
(45) Date of Patent: Feb. 1, 2022

(54) INFORMATION PROCESSING APPARATUS AND INFORMATION PROCESSING METHOD

(71) Applicant: SONY CORPORATION, Tokyo (JP)

(72) Inventors: Shingo Takamatsu, Tokyo (JP); Naoto Tsuboi, Kanagawa (JP); Kazuki Yoshiyama, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 387 days.

(21) Appl. No.: 15/528,600

(22) PCT Filed: Aug. 26, 2015

(86) PCT No.: PCT/JP2015/073998
§ 371 (c)(1),
(2) Date: May 22, 2017

(87) PCT Pub. No.: WO2016/088413
PCT Pub. Date: Jun. 9, 2016

(65) Prior Publication Data
US 2017/0265817 A1    Sep. 21, 2017

(30) Foreign Application Priority Data
Dec. 4, 2014  (JP) .............................. JP2014-245904

(51) Int. Cl.
*A61B 5/00*      (2006.01)
*A61B 5/11*      (2006.01)
(Continued)

(52) U.S. Cl.
CPC .............. *A61B 5/7275* (2013.01); *A61B 5/00* (2013.01); *A61B 5/11* (2013.01); *A61B 5/1112* (2013.01);
(Continued)

(58) Field of Classification Search
CPC ..... A61B 5/7275; A61B 5/681; A61B 5/1118; A61B 5/11; A61B 5/6824; A61B 5/742; A61B 2560/0242; G16H 50/30
(Continued)

(56) References Cited

U.S. PATENT DOCUMENTS 6,292,687 B1 *  9/2001  Lowell ................. A61B 5/1112
                                                    600/515
9,173,596 B1 *  11/2015 Berme ................ G06F 19/3481
(Continued)

FOREIGN PATENT DOCUMENTS

| JP | 2013-085896 A | 5/2013 |
| JP | 2013-210869 A | 10/2013 |
| JP | 2013-238970 A | 11/2013 |

OTHER PUBLICATIONS

"Sending Platform Service that Contributes to Field Innovation", Fujitsu, Jul. 2009, vol. 60, No. 4, pp. 358-362.
"Sensing Platform Service that Contributes to Field Innovation", Fujitsu, vol. 60, No. 4, Jul. 2009, 358-362 pages.

*Primary Examiner* — May A Abouelela
(74) *Attorney, Agent, or Firm* — Chip Law Group

(57) ABSTRACT

An information processing apparatus is provided which includes a sensor information acquisition unit that acquires sensor information including at least biological information of a user and a biological information change prediction unit that predicts a change of the biological information from the sensor information in accordance with a framework based on knowledge concerning poor physical condition of the user.

10 Claims, 8 Drawing Sheets

(51) Int. Cl.
*G16H 10/60* (2018.01)
*G16H 40/63* (2018.01)
*G16H 50/50* (2018.01)
*G16H 50/20* (2018.01)
*G16H 40/67* (2018.01)

(52) U.S. Cl.
CPC ............ *A61B 5/1118* (2013.01); *A61B 5/681* (2013.01); *A61B 5/6824* (2013.01); *A61B 5/742* (2013.01); *G16H 10/60* (2018.01); *G16H 40/63* (2018.01); *G16H 40/67* (2018.01); *G16H 50/20* (2018.01); *G16H 50/50* (2018.01); *A61B 2560/0242* (2013.01)

(58) Field of Classification Search
USPC .................................................. 600/587, 595
See application file for complete search history.

(56) References Cited

U.S. PATENT DOCUMENTS

| | | | |
|---|---|---|---|
| 2002/0188214 | A1* | 12/2002 | Misczynski .......... A61B 5/0006 600/516 |
| 2011/0237924 | A1* | 9/2011 | McGusty ........... A61B 5/04085 600/391 |
| 2012/0084054 | A1* | 4/2012 | Yuen .................... A61B 5/0002 702/160 |
| 2014/0375461 | A1* | 12/2014 | Richardson ........ G08B 21/0446 340/573.7 |
| 2015/0164349 | A1* | 6/2015 | Gopalakrishnan .......................... A61B 5/02405 600/508 |
| 2015/0258415 | A1* | 9/2015 | Trivedi ............. H04M 1/72522 700/91 |
| 2015/0305675 | A1* | 10/2015 | Miller ................. A61B 5/6823 600/301 |
| 2015/0351690 | A1* | 12/2015 | Toth .................... A61B 5/6833 600/373 |

\* cited by examiner

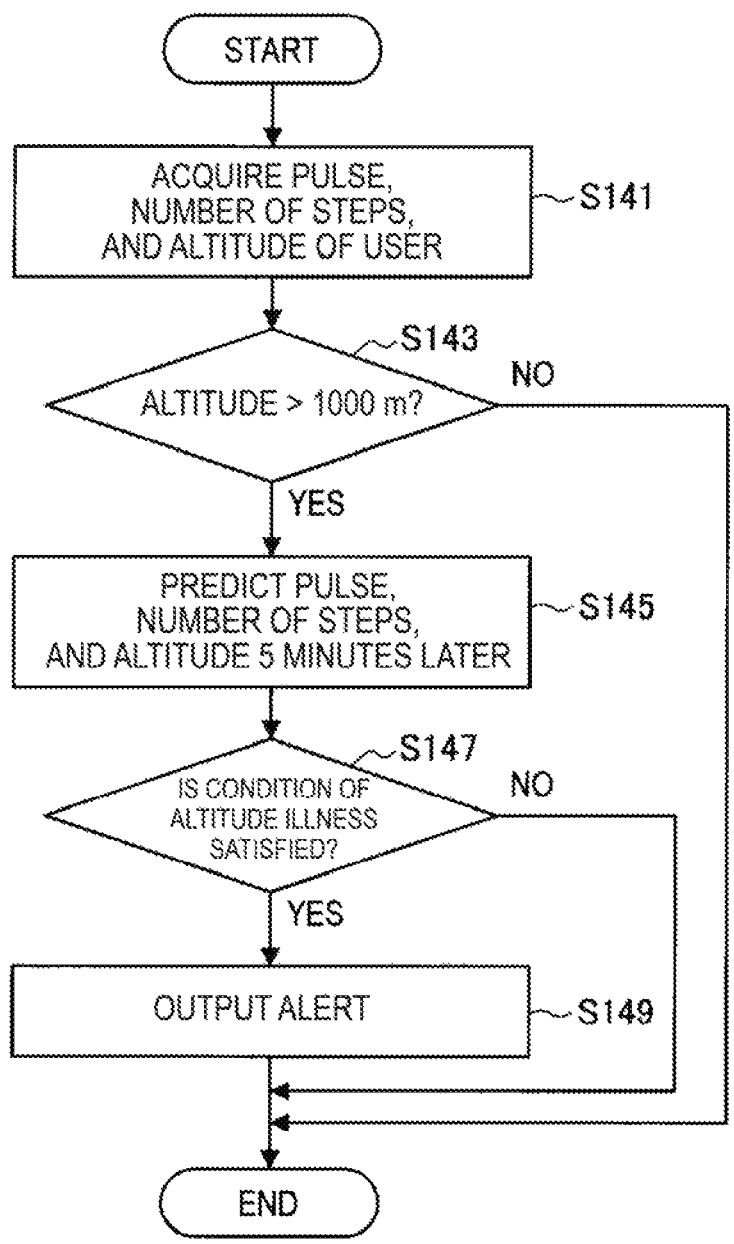

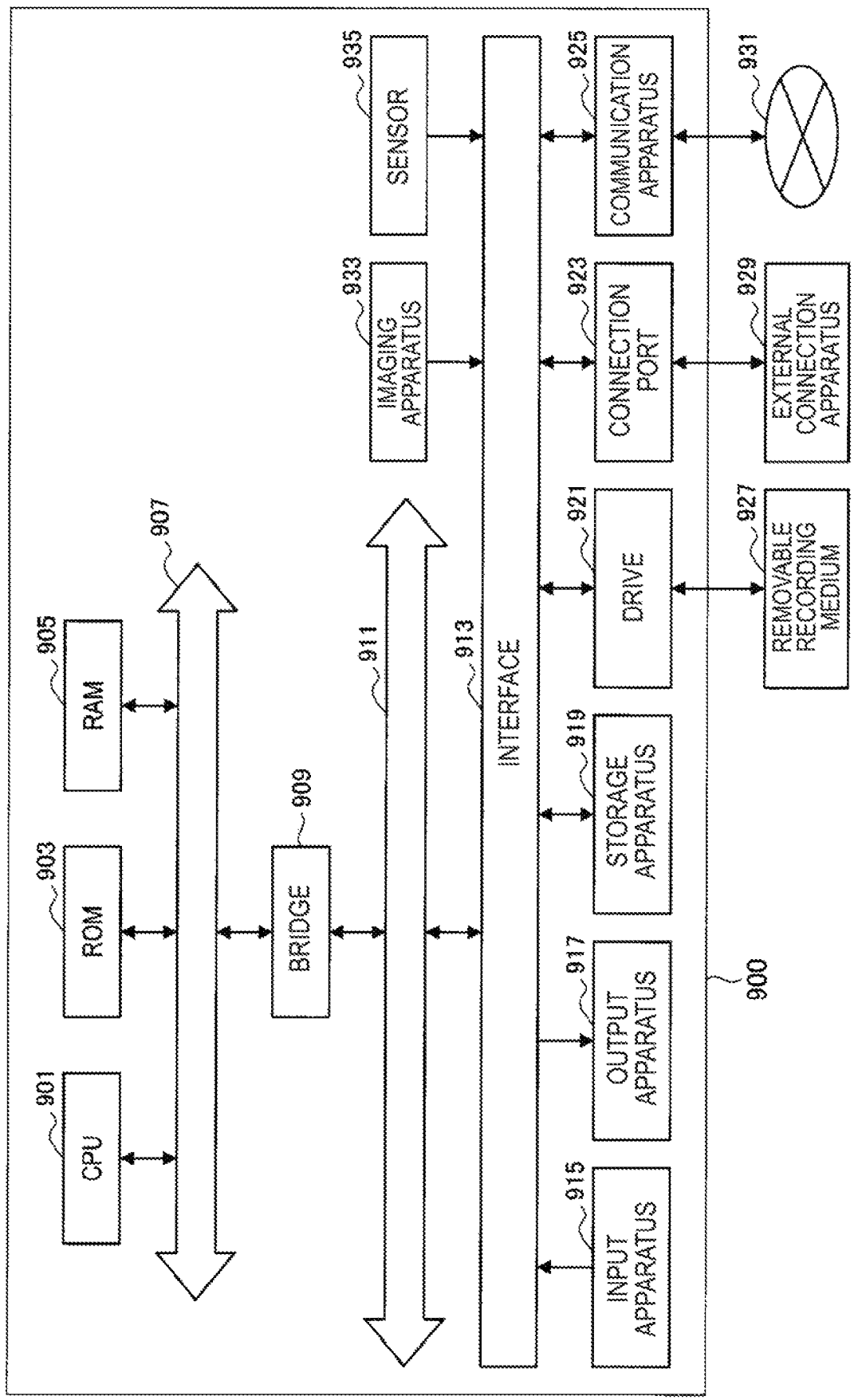

INFORMATION PROCESSING APPARATUS AND INFORMATION PROCESSING METHOD

CROSS REFERENCE TO RELATED APPLICATIONS

This application is a U.S. National Phase of International Patent Application No. PCT/JP2015/073998 filed on Aug. 26, 2015, which claims priority benefit of Japanese Patent Application No. JP 2014-245904 filed in the Japan Patent Office on Dec. 4, 2014. Each of the above-referenced applications is hereby incorporated herein by reference in its entirety.

TECHNICAL FIELD

The present disclosure relates to an information processing apparatus, an information processing method, and a program.

BACKGROUND ART

These days, the acquisition of various pieces of information concerning a user using a sensor mounted on a wearable terminal or the like is commonly performed. The information to be acquired includes, for example, the biological information of the user such as the pulse and the body temperature. Various technologies that use such information to provide useful information for the user are proposed. For example, Patent Literature 1 describes a technology that acquires biological information concerning the biological clock of a user and assists the action of the user for bringing the biological clock close to an ideal state.

CITATION LIST

Patent Literature

Patent Literature 1: JP 2013-210869A

DISCLOSURE OF INVENTION

Technical Problem

In the technology described in Patent Literature 1, biological information is treated as information corresponding to the phase of the biological clock of the user, for example. Thus, for regularly changing conditions of the user, it is not necessarily difficult to predict them on the basis of biological information or to make a proposal for improving them. However, the condition of the user does not necessarily change regularly, and there are changes occurring irregularly. For example, changes in condition that are recognized as poor physical condition by the user are often irregular changes. Technology that makes it possible to predict such changes is not yet proposed to a sufficient degree.

Thus, the present disclosure proposes a new and improved information processing apparatus, a new and improved information processing method, and a new and improved program that can predict the change in the condition of the user in a wider range.

Solution to Problem

According to the present disclosure, there is provided an information processing apparatus including: a sensor information acquisition unit configured to acquire sensor information including at least biological information of a user; and a biological information change prediction unit configured to predict a change of the biological information from the sensor information in accordance with a framework based on knowledge concerning poor physical condition of the user.

In addition, according to the present disclosure, there is provided an information processing method including: acquiring sensor information including at least biological information of a user; and predicting a change of the biological information from the sensor information in accordance with a framework based on knowledge concerning poor physical condition of the user.

In addition, according to the present disclosure, there is provided a program for causing a computer to execute: a function of acquiring sensor information including at least biological information of a user; and a function of predicting a change of the biological information from the sensor information in accordance with a framework based on knowledge concerning poor physical condition of the user.

Advantageous Effects of Invention

As described above, according to the present disclosure, the change in the condition of the user can be predicted in a wider range.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 5 is a flow chart showing an example of the processing that predicts the occurrence of altitude illness in an embodiment of the present disclosure.

FIG. 9 is a block diagram showing an example of the hardware configuration of an information processing apparatus according to an embodiment of the present disclosure.

MODE(S) FOR CARRYING OUT THE INVENTION

Figure 1:
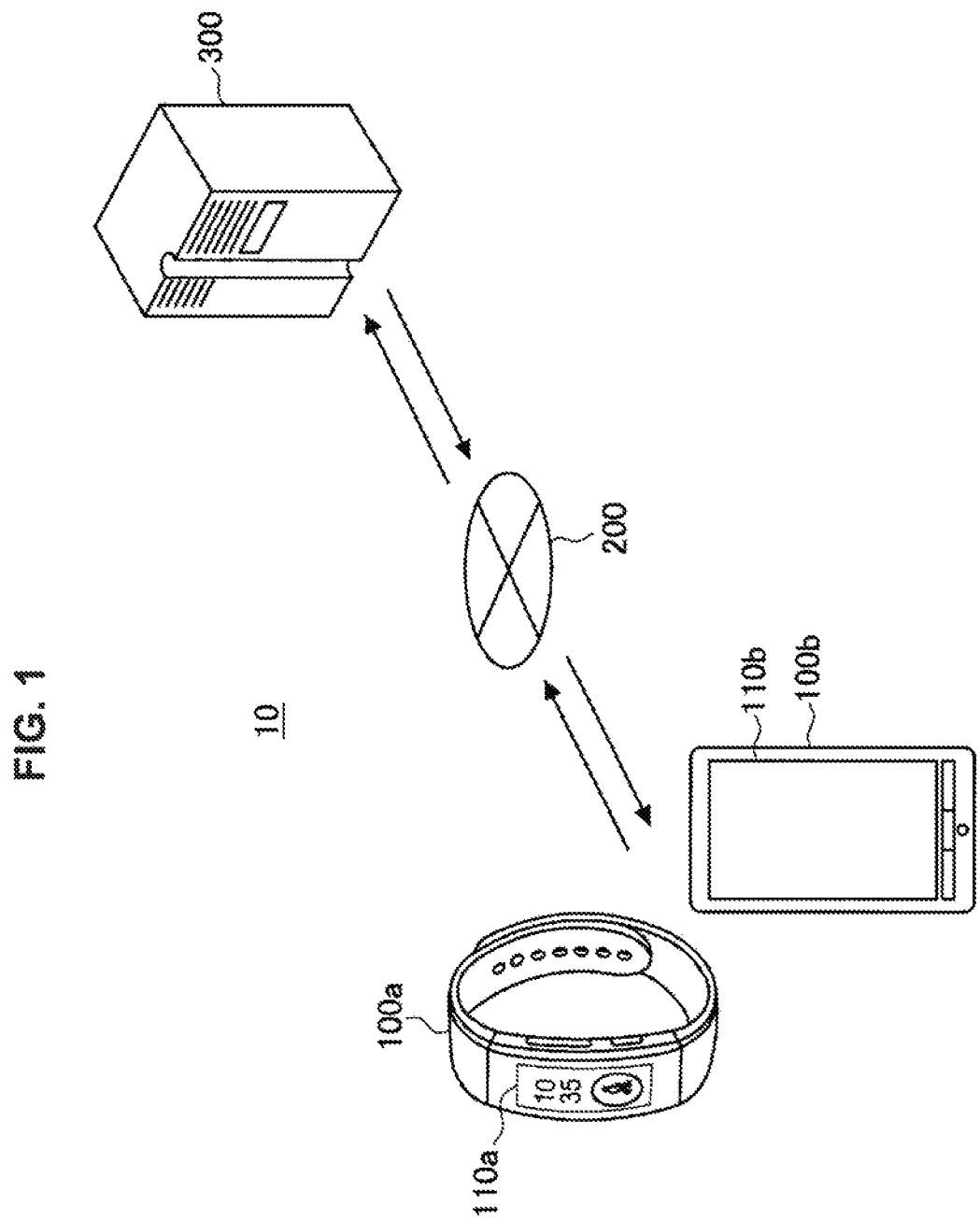
FIG. 1 is a diagram showing a rough configuration of a system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description is given in the following order.
1. System configuration
2. Configuration of server
3. Specific example regarding prediction of occurrence of altitude illness
3-1. Conversion of sensor information
3-2. Prediction of biological information change using model
3-3. Prediction of occurrence of altitude illness
3-4. Examples of action assistance information
4. Modification examples
5. Hardware configuration
6. Supplement

1. SYSTEM CONFIGURATION

FIG. 1 is a diagram showing a rough configuration of a system according to an embodiment of the present disclosure. With reference to FIG. 1, a system 10 includes a terminal apparatus 100 and a server 300. The terminal apparatus 100 and the server 300 are connected by a network 200. Each component will now be further described.

The terminal apparatus 100 includes at least one device that is carried with or worn on the user. In FIG. 1, a piece of wristwear 100a and a smartphone 100b are shown as an example of the terminal apparatus 100. The terminal apparatus 100 may include, as well as the piece of wristwear 100a, another wearable terminal device such as an eyewear article. Further, the terminal apparatus 100 may include, as well as the smartphone 100b, another mobile terminal device such as a tablet. The terminal apparatuses 100 of these components is obtained using, for example, a hardware configuration of an information processing apparatus like that described later.

In the present embodiment, the terminal apparatus 100 has the function of acquiring sensor information concerning the user and the function of providing the user with action assistance information generated on the basis of the sensor information. These functions may be implemented by the same terminal apparatus 100, or may be implemented by terminal apparatuses 100 different from each other. For example, in the system 10, the piece of wristwear 100a may acquire sensor information, and the smartphone 100b may provide action assistance information. Alternatively, both of the piece of wristwear 100a and the smartphone 100b may acquire sensor information and furthermore provide action assistance information.

The terminal apparatus 100 includes various sensors in order to acquire sensor information. For example, the terminal apparatus 100 includes sensors for detecting the biological information of the user, more specifically, the pulse, blood oxygen content, perspiration, body temperature, etc. Such sensors may be installed in the piece of wristwear 100a, for example. Further, the terminal apparatus 100 may include sensors for detecting physical information showing the physical behavior of the user, more specifically, the acceleration, angular velocity, etc. Such sensors may be installed in either of the piece of wristwear 100a and the smartphone 100b. Further, the terminal apparatus 100 may include sensors for detecting the information of the environment around the user, more specifically, the atmospheric pressure, atmospheric temperature, humidity, sound, light, etc. Further, the terminal apparatus 100 may include a sensor for detecting the location information of the user, such as a global positioning system (GPS) receiver. Such sensors may be installed in the piece of wristwear 100a or the smartphone 100b in accordance with the respective objects to be detected. Specific configurations of these sensors are already well known, and a description is omitted. In the present embodiment, suitable sensors among various known sensors are installed in the terminal apparatus 100 in order to acquire sensor information like the above, for example.

On the other hand, the terminal apparatus 100 includes an output apparatus in order to provide action assistance information. For example, the terminal apparatus 100 includes a display for displaying action assistance information as an image. In the example shown in FIG. 1, a display 110a is provided in the piece of wristwear 100a, and a display 110b is provided in the smartphone 100b. The terminal apparatus 100 may also include a speaker for outputting action assistance information as voice, a vibrator for expressing action assistance information as vibration, or the like, for example. The terminal apparatus 100 may output action assistance information also by combining a plurality of types of output apparatuses.

As described above, in the present embodiment, the individual terminal apparatus 100 may implement only one of the acquisition of sensor information and the provision of action assistance information. Therefore, the terminal apparatus 100 is not necessarily limited to an example like the piece of wristwear 100a and the smartphone 100b shown in FIG. 1, and a sensing-dedicated terminal not including an output apparatus or an output-dedicated terminal not including a sensor may be included in the terminal apparatus 100, for example. Here, the output-dedicated terminal may include a device that is not necessarily carried with or worn on the user, such as a desktop (nonportable) personal computer.

The server 300 is one or a plurality of devices that provide service to the terminal apparatus 100. Although in FIG. 1 the server 300 is illustrated as a single device, in another example the server 300 may be formed by the cooperation of a plurality of devices connected to the network 200. The server 300 is not limited to a device operated by a service provider, and may include a terminal apparatus possessed by the user, such as a personal computer installed in the home by the user. Alternatively, part of the functions of the server 300 may be implemented by the interior of a device that is carried with or worn on the user. In the example shown in FIG. 1, the smartphone 100b may implement part of the functions of the server 300. The one device or each of the plurality of devices forming the server 300 is obtained by a hardware configuration of an information processing apparatus like that described later, for example.

The network 200 includes various wired or wireless networks. In the example of FIG. 1, the piece of wristwear 100a communicates with the smartphone 100b by Bluetooth (registered trademark), and the smartphone 100b communicates with the server 300 via a mobile network or the Internet. Thus, the network 200 may not only connect the terminal apparatus 100 and the server 300, but also mutually connect a plurality of terminal apparatuses 100 or mutually connect a plurality of devices constituting the server 300.

2. CONFIGURATION OF SERVER

Figure 2:
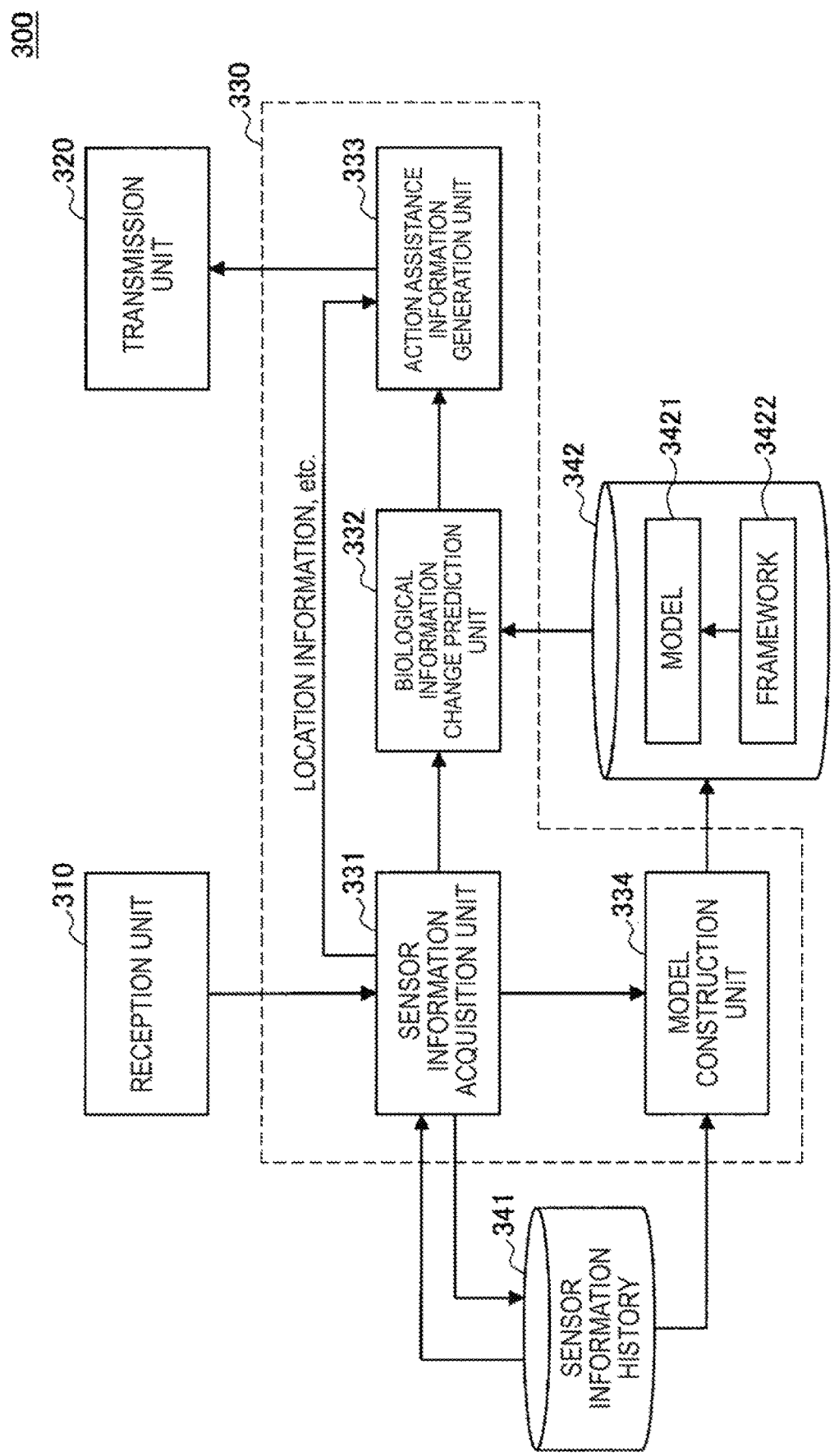
FIG. 2 is a block diagram showing a rough functional configuration of a server according to an embodiment of the present disclosure.

FIG. 2 is a block diagram showing a rough functional configuration of a server according to an embodiment of the present disclosure. With reference to FIG. 2, the server 300 includes a reception unit 310, a transmission unit 320, and a processing unit 330. The reception unit 310 and the transmission unit 320 are formed of various communication apparatuses that communicate with the terminal apparatus 100 via the network 200. The processing unit 330 is formed of a processor such as a central processing unit (CPU). The processor forming the processing unit 330 operates in accordance with a program stored in a memory or a storage, and thereby the functions of a sensor information acquisition unit 331, a biological information change prediction unit 332, an action assistance information generation unit 333, and a model construction unit 334 are implemented. The processing unit 330 refers to a sensor information history 341 and a prediction rule 342 stored in a memory or a storage. Each component will now be further described.

The sensor information acquisition unit 331 implements an interface function that acquires sensor information received by the reception unit 310 from the terminal apparatus 100. In the present embodiment, the sensor information includes at least the biological information of the user who carries or wear the terminal apparatus 100. As described above in regard to the terminal apparatus 100, the biological information may include the pulse, blood oxygen content, perspiration, body temperature, etc. The sensor information may include physical information showing the physical behavior of the user. The physical information may include the acceleration, angular velocity, etc. The sensor information may include the information of the environment around the user. The environmental information may include, for example, the atmospheric pressure, atmospheric temperature, humidity, sound, light, etc. The sensor information may also include the location information of the user acquired using the GPS or the like.

Further, the sensor information acquisition unit 331 may implement a function that converts the acquired sensor information to a form suitable for use in the biological information change prediction unit 332 described later. More specifically, the sensor information acquisition unit 331 adjusts the sampling interval of measurement values to be included in the sensor information etc., and extracts other information from one or a plurality of pieces of information included in the sensor information. For example, the sensor information acquisition unit 331 may estimate the walking state of the user on the basis of the acceleration and/or the angular velocity included in the physical information. The walking state may be expressed by the number of steps per hour, for example. In the estimation, the sensor information acquisition unit 331 may refer to not only the latest sensor information but also past sensor information acquired from the sensor information history 341. Further, the sensor information acquisition unit 331 may estimate the altitude of the user on the basis of the atmospheric pressure included in the environmental information, for example. In the present specification, also information such as the walking state and the altitude mentioned above is treated as a type of sensor information to the extent that it is extracted from the sensor information.

The biological information change prediction unit 332 predicts the change of the biological information of the user from the sensor information acquired by the sensor information acquisition unit 331. As described above, in the present embodiment, biological information is included in the sensor information, and further physical information, environmental information, etc. may be included. Therefore, it can also be said that the biological information change prediction unit 332 predicts the change of the biological information at or after a certain time point on the basis of biological information acquired until then and additional information such as physical information and environmental information. In the present embodiment, the biological information change prediction unit 332 executes prediction in accordance with a framework 3422 included in the prediction rule 342. The framework 3422 is configured on the basis of knowledge concerning the poor physical condition of the user. More specifically, the biological information change prediction unit 332 predicts the change of the biological information using a model 3421 constructed in accordance with the framework 3422. Here, as described above, the framework 3422 is configured on the basis of knowledge concerning the poor physical condition of the user; therefore, the biological information change prediction unit 332 can predict the occurrence of poor physical condition of the user on the basis of the change of the biological information. A more specific example of the framework 3422 and the model 3421 is described later.

The action assistance information generation unit 333 generates action assistance information for the user in accordance with the result of prediction by the biological information change prediction unit 332. For example, when the occurrence of poor physical condition of the user is predicted by the biological information change prediction unit 332, the action assistance information generation unit 333 generates action assistance information for the user's avoiding poor physical condition. More specifically, when the biological information change prediction unit 332 has predicted the occurrence of altitude illness of the user, the action assistance information generation unit 333 generates information that recommends to the user taking a rest or reducing the altitude. When generating information, the action assistance information generation unit 333 may use the sensor information acquired by the sensor information acquisition unit 331. For example, when the occurrence of altitude illness is predicted during mountain climbing, the action assistance information generation unit 333 may inform the user of the nearest mountain lodge using the location information of the user included in the sensor information. As another example, when the biological information change prediction unit 332 has predicted the occurrence of motion sickness of the user, the action assistance information generation unit 333 may generate information that recommends to the user opening the window or looking in the distance. In this case, in order to check until when the user continues to ride in the vehicle, the information of the schedule of the user may be acquired from the terminal apparatus 100 or the like. The information generated by the action assistance information generation unit 333 is transmitted to the terminal apparatus 100 via the transmission unit 320. Also a specific example of the action assistance information generated by the action assistance information generation unit 333 is described later.

The model construction unit 334 constructs the model 3421 on the basis of the sensor information history 341 and in accordance with the framework 3422. The sensor information history 341 is the history of the sensor information acquired by the sensor information acquisition unit 331. The sensor information may be accumulated in the sensor information history 341 in the form as it is when acquired, or may be accumulated in the sensor information history 341 after undergoing processing by the sensor information acquisition unit 331 like that described above, for example. Further, the model construction unit 334 may update the model 3421 on the basis of the latest sensor information acquired by the sensor information acquisition unit 331. The model construction unit 334 constructs the model 3421 on the basis of the result of machine learning executed in accordance with the framework 3422, for example. In the present embodiment, the framework 3422 specifies information that is factors in the change of the biological information from information other than the biological information included in the sensor information. For example, the model construction unit 334 executes machine learning for the change of the biological information of the user that occurred in the past, which change is shown by the sensor information history 341, using, as factors, the information specified by the framework 3422, and estimates the parameters of the model 3421.

Here, as described above, the framework 3422 is configured on the basis of knowledge concerning the poor physical condition of the user. Therefore, in the above case, in the machine learning that the model construction unit 334 executes in accordance with the framework 3422, the factors in the change of the biological information are narrowed down in advance on the basis of the type of poor physical condition desired to be predicted. For example, the framework 3422 configured on the basis of knowledge concerning altitude illness specifies, as factors in the change of the biological information, the walking state of the user estimated on the basis of the acceleration and/or the angular velocity included in the sensor information (more specifically, the number of steps per hour) and the altitude of the user estimated on the basis of the atmospheric pressure included in the sensor information. In this case, the model construction unit 334 extracts the information of the pulse, the walking state, and the altitude from the sensor information history, and constructs a model of pulse change using the walking state and the altitude as factors.

Thus, the model construction unit 334 constructs the model 3421 in accordance with the framework 3422; thereby, a model with high appropriateness in which factors that are estimated as having high relevance from experiential or pathological knowledge are selectively incorporated can be constructed in accordance with the type of poor physical condition of which the occurrence is desired to be predicted (altitude illness, motion sickness, heatstroke, dehydration during exercise, etc.), for example. From the viewpoint of making a model, the change of the biological information of the user occurs due to various factors, and it is not easy to make a model while covering all the factors. However, when it is attempted to predict the occurrence of a specified type of poor physical condition, a model with high appropriateness can be constructed by utilizing experiential or pathological knowledge like the above. On the other hand, from the viewpoint of knowledge, even when factors in poor physical condition are specified experientially or pathologically, it is not possible to predict the occurrence of poor physical condition in real time. The prediction of the occurrence of poor physical condition is enabled by constructing the model 3421 in accordance with the framework 3422 based on knowledge in the above manner.

In the following, the prediction of the change of the biological information of the user and the provision of action assistance information based on the prediction performed in the system 10 like the above are further described using the case of the prediction of the occurrence of altitude illness as a specific example.

3. SPECIFIC EXAMPLE REGARDING PREDICTION OF OCCURRENCE OF ALTITUDE ILLNESS

In this example, in the system 10, the piece of wristwear 100a includes sensors that detect the pulse and the blood oxygen content of the user. Further, the smartphone 100b includes sensors that detect the acceleration, the angular velocity, and the atmospheric pressure. Therefore, in this example, sensor information that includes the pulse and the blood oxygen content as biological information, the acceleration and the angular velocity as physical information, and the atmospheric pressure as environmental information is transmitted from the terminal apparatus 100 to the server 300. In the server 300, the sensor information acquisition unit 331 estimates the number of steps per hour of the user from the acceleration and the angular velocity of the sensor information, and estimates the altitude of the user from the atmospheric pressure. The biological information change prediction unit 332 predicts the occurrence of altitude illness on the basis of the information of the pulse, the blood oxygen content, the number of steps, and the altitude of the user acquired in this manner. In the following, first, the conversion of sensor information by the sensor information acquisition unit 331 like the above (from the acceleration and the angular velocity to the number of steps and from the atmospheric pressure to the altitude) is described using the case of the number of steps as an example.

(3-1. Conversion of Sensor Information)

Figure 3:
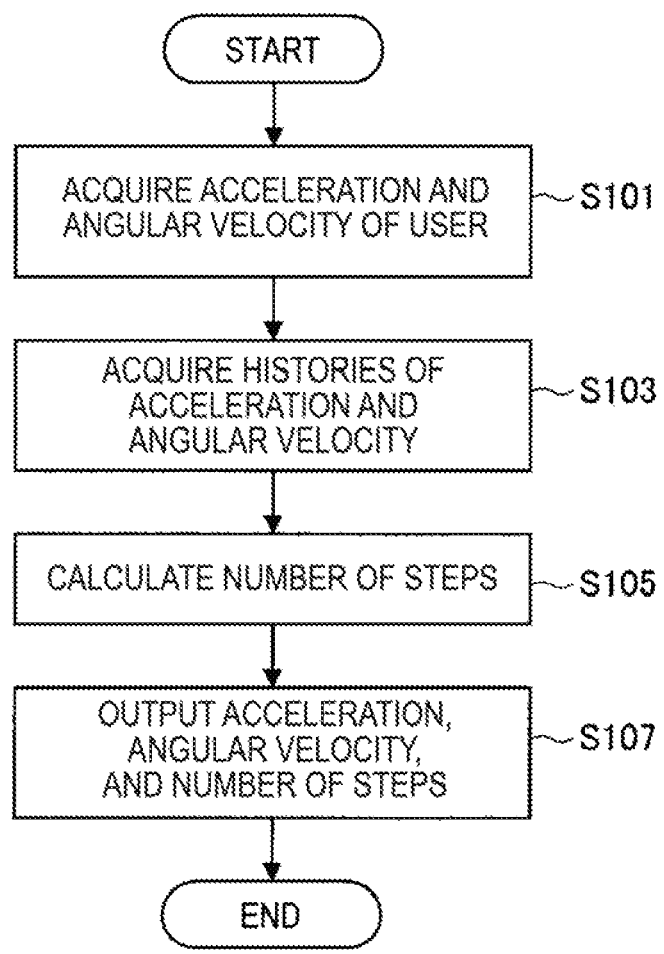
FIG. 3 is a flow chart showing an example of the processing that converts the acceleration and the angular velocity to the number of steps in an embodiment of the present disclosure.

FIG. 3 is a flow chart showing an example of the processing that converts the acceleration and the angular velocity to the number of steps in an embodiment of the present disclosure. With reference to FIG. 3, the sensor information acquisition unit 331 acquires, at a certain time point, the information of the acceleration and the angular velocity of the user (S101). The sensor information acquisition unit 331 further acquires the histories of the acceleration and the angular velocity from the sensor information history 341 (S103). In order to estimate the number of steps of the user in a predetermined length of time including the past, the sensor information acquisition unit refers to the histories of the acceleration and the angular velocity in the estimation of the number of steps.

Next, the sensor information acquisition unit 331 calculates the number of steps per hour on the basis of the acceleration and the angular velocity acquired in S101 and the histories of the acceleration and the angular velocity acquired in S103 (S105). Further, the sensor information acquisition unit 331 outputs, in addition to the calculated number of steps, the information of the acceleration and the angular velocity used as the basis (S107). The information of the number of steps is outputted to the biological information change prediction unit 332, and is used for the prediction of the change of the biological information (the pulse and the blood oxygen content) like that described later. Further, the information of the number of steps may also be stored in the sensor information history 341, and may be used as learning data for the construction of the model 3421 by the model construction unit 334. On the other hand, the information of the acceleration and the angular velocity is stored in the sensor information history 341, and is used to estimate the number of steps on the basis of the acceleration and the angular velocity that are acquired at a later time.

(3-2. Prediction of Biological Information Change Using Model)

Next, the prediction of the change of the biological information using the model 3421 by the biological information change prediction unit 332 is described. In the following description, for the sake of simplicity, it is assumed that the time point $t_0$ of the start of measurement, the sampling interval $\Delta t$, and the number of samples n (n=1, 2, . . . ) coincide between the pulse, the blood oxygen content, the number of steps, and the altitude of the user included in the sensor information. In the case where these are different, processing such as resampling by the sensor information acquisition unit 331 is performed. Here, the respective pieces of information (the measurement values) included in the sensor information at time $t_k$ are denoted by pulse $s_P(t_k)$, blood oxygen content $s_O(t_k)$, the number of steps $s_S(t_k)$, and altitude $s_H(t_k)$. Time $t_k$ means $t_0+k\Delta t$ (k=0, 1, . . . , n). Using these symbols, time-series data provided as sensor information, that is, the pulse $S_P$, the blood oxygen content $S_O$, the number of steps $S_S$, and the altitude $S_H$ of the user are defined by Formula 1 below.

(Formula 1)

$$S_P=\{(t_k,s_P(t_k))|k=0,1,\ldots,n\},$$

$$S_O=\{(t_k,s_O(t_k))|k=0,1,\ldots,n\},$$

$$S_S=\{(t_k,s_S(t_k))|k=0,1,\ldots,n\},$$

$$S_H=\{(t_k,s_H(t_k))|k=0,1,\ldots,n\}, \quad \text{[Math. 1]}$$

In this example, the model 3421 includes a model like Formula 2 below regarding the predicted value of the pulse $s_P(t_{k+1})$. The parameter vector $W_P$ is estimated by processing of machine learning by the model construction unit 334 like that described later, and may be periodically updated on the basis of the latest sensor information. In the case of k=0, it is assumed that $s_P(t_{k-1})=s_S(t_{k-1})=s_H(t_{k-1})=0$.

(Formula 2)

$$s_P(t_{k+1}) = W_P \cdot X_P(t_k), \quad \text{[Math. 2]}$$
$$W_P = (w_{PP1}, w_{PP2}, w_{PS1}, w_{PS2}, w_{PH1}, w_{PH2}, w_{PC}),$$

$$X_P(t_k) = \begin{pmatrix} s_P(t_k) \\ s_P(t_k) - s_P(t_{k-1}) \\ s_S(t_k) \\ s_S(t_k) - s_S(t_{k-1}) \\ s_H(t_k) \\ s_H(t_k) - s_H(t_{k-1}) \\ 1.0 \end{pmatrix}$$

Further, in this example, the model 3421 includes the model of Formula 3 below regarding the predicted value of the blood oxygen content $s_O(t_{k+1})$. The parameter vector $W_O$ is estimated by processing of machine learning by the model construction unit 334, and may be periodically updated on the basis of the latest sensor information, like in the case of the pulse mentioned above. In the case of k=0, it is assumed that $s_O(t_{k-1})=s_S(t_{k-1})=s_H(t_{k-1})=0$.

(Formula 3)

$$s_O(t_{k+1}) = W_O \cdot X_O(t_k), \quad \text{[Math. 3]}$$
$$W_O = (w_{OO1}, w_{OO2}, w_{OS1}, w_{OS2}, w_{OH1}, w_{OH2}, w_{OC}),$$

$$X_O(t_k) = \begin{pmatrix} s_O(t_k) \\ s_O(t_k) - s_O(t_{k-1}) \\ s_S(t_k) \\ s_S(t_k) - s_S(t_{k-1}) \\ s_H(t_k) \\ s_H(t_k) - s_H(t_{k-1}) \\ 1.0 \end{pmatrix}$$

Further, the model 3421 includes also models for the predicted value of the number of steps $s_S(t_{k+1})$ and the predicted value of the altitude $s_H(t_{k+1})$. In this example, these models are auto-regressive (AR) models for the number of steps $s_S(t_k)$ and the altitude $s_H(t_k)$. An AR model is known and a detailed description is omitted; the AR model can estimate the parameter by machine learning based on the sensor information history 341.

The biological information change prediction unit 332 can predict the change of the biological information from time $t_n$ to time $t_{n+p}$ (p=1, 2, . . . ) using the model 3421 like the above recursively. How far a time in the future to set time $t_{n+p}$ to is determined with consideration of the precision of the model 3421, the time necessary for the action (recommended by action assistance information) that the user takes in order to avoid altitude illness when the occurrence of altitude illness is predicted, etc., for example. As an example, time $t_{n+p}$ may be five minutes after time $t_n$.

The model 3421 used in the prediction mentioned above is constructed by the model construction unit 334 performing machine learning based on the sensor information history 341. More specifically, the model construction unit 334 estimates the parameters of the model 3421 serving as the factors specified by the framework 3422 by machine learning based on the sensor information history 341. In other words, Formula 2 and Formula 3 described in the above and the AR models regarding the number of steps and the altitude are already defined by the framework 3422, and the model construction unit 334 estimates the parameters $W_P$ and $W_O$ and the parameters of the AR models by machine learning.

Here, the model construction unit 334 generates training data for machine learning from a set of data included in the sensor information history 341, that is, the pulse $S_P$, the blood oxygen content $S_O$, the number of steps $S_S$, and the altitude $S_H$ of the user. Each of the training data $S'_P$, $S'_O$, $S'_S$, and $S'_H$ is defined by Formula 4 below, for example. How far a time in the past to set time $t_{n-q}$ to is determined with consideration of the needed precision of the model 3421, the period of the change of the characteristics (physical constitution) of the user regarding the biological information, etc., for example. As an example, time $t_{n-q}$ may be set to three months before time $t_n$.

(Formula 4)

$$S'_P=\{(s_P(t_{k+1}),X_P(t_k))|k=n-q,\ldots,n-2,n-1\},$$

$$S'_O=\{(s_O(t_{k+1}),X_O(t_k))|k=n-q,\ldots,n-2,n-1\},$$

$$S'_S=\{(s_S(t_{k+1}))|k=n-q,\ldots,n-2,n-1\},$$

$$S'_H=\{(s_H(t_{k+1}))|k=n-q,\ldots,n-2,n-1\}, \quad \text{[Math. 4]}$$

In this example, the framework 3422 is configured on the basis of knowledge concerning altitude illness. Altitude illness is defined as an oxygen shortage state that occurs at a certain time point due to a rapid increase in altitude caused by mountain climbing, for example. In the event of altitude illness, the pulse increases and the blood oxygen content decreases due to the oxygen shortage state. In other words, the symptom of altitude illness may be detected as changes of the pulse and the blood oxygen content, which are biological information. On the other hand, mountain climbing, which is a cause of altitude illness, is defined as a state in which the number of steps increases continuously due to walking and the altitude increases. The model 3421 like that described above is constructed by the framework 3422 configured on the basis of knowledge.

Figure 4:
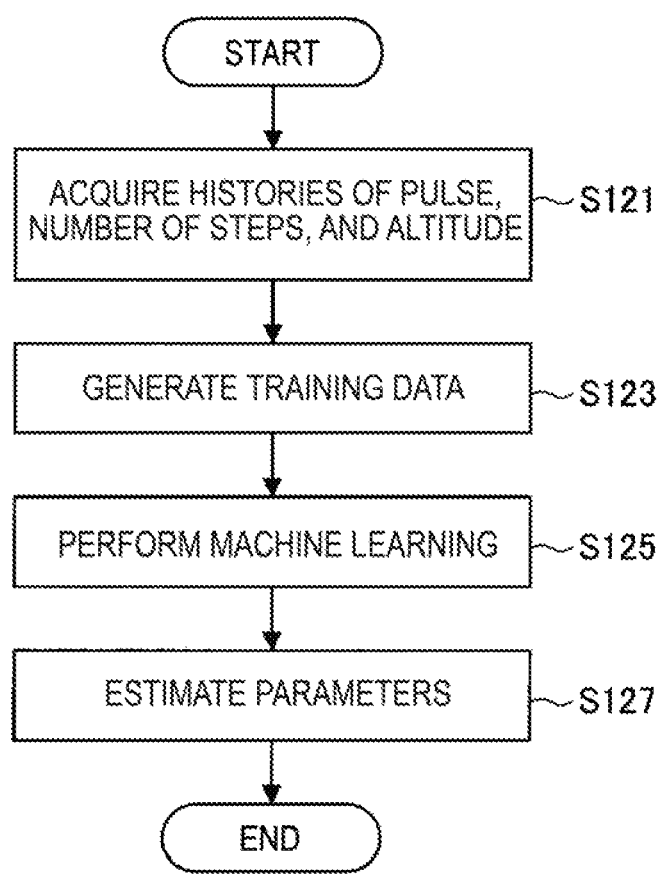
FIG. 4 is a flow chart showing an example of the processing that constructs a model of pulse change in an embodiment of the present disclosure.

FIG. 4 is a flow chart showing an example of the processing that constructs a model of pulse change in an embodiment of the present disclosure. With reference to FIG. 4, the model construction unit 334 first acquires the histories $S_P$, $S_S$, and $S_H$ of the pulse, the number of steps, and the altitude from the sensor information history 341 (S121). The model construction unit 334 generates training data $S'_P$ on the basis of these histories (S123). The histories of the number of steps and the altitude are incorporated in the training data $S'_P$ as the vector $X_P(t_k)$. Next, the model construction unit 334 performs machine learning using the training data $S'_P$ (S125). For the method of machine learning, various methods are already well known, and a detailed description is omitted. In the present embodiment, a suitable method among them may be used.

The model construction unit 334 estimates the parameter vector $W_P$ of the model of pulse change on the basis of the result of machine learning (S127). Also the parameter vector $W_O$ of the model of blood oxygen content change and the parameters of the AR models are estimated in a similar manner. Thus, the biological information change prediction unit 332 can predict the change of the pulse and the blood oxygen content using the model 3421.

(3-3. Prediction of Occurrence of Altitude Illness)

Further, the biological information change prediction unit 332 predicts the occurrence of altitude illness on the basis of the predicted change of the pulse and the blood oxygen content. More specifically, the biological information change prediction unit 332 predicts the occurrence of altitude illness in accordance with a condition composed of the predicted values $s_P(t_{n+p})$ and $s_O(t_{n+p})$ of the pulse and the blood oxygen content at time $t_{n+p}$. In the following description, time $t_{n+p}$ is set to five minutes after time to for the sake of convenience.

Here, the condition for predicting the occurrence of altitude illness may be extracted from the accumulation of measurement values of the pulse and the blood oxygen content in the case where the user has actually suffered from altitude illness. The condition is statistically extracted from sensor information provided by a large number of users, for example. The biological information change prediction unit 332 specifies the relationship between the measurement values of the pulse and the blood oxygen content and the occurrence of altitude illness using a linear regression model or a decision tree, for example.

Here, in order to specify, in the past information, the case where the user has suffered from altitude illness, some information other than the biological information is used. For example, when the user has suffered from altitude illness during mountain climbing, the user may input this event to the terminal apparatus 100 as information. In this case, a label indicating the occurrence of altitude illness is attached to the sensor information that is transmitted to the server 300. Alternatively, when the fact that the user has sat down during mountain climbing or the like is detected on the basis of the acceleration and the angular velocity included in the sensor information, the server 300 may detect the occurrence of altitude illness automatically.

Further, when predicting the occurrence of altitude illness, the biological information change prediction unit 332 may refer to information other than the prediction of the change of the biological information. For example, when reference to the predicted value of the altitude $s_H(t_{k+1})$ shows that the altitude is less than 1000 m, the biological information change prediction unit 332 may assess the event as not altitude illness regardless of the biological information.

FIG. 5 is a flow chart showing an example of the processing that predicts the occurrence of altitude illness in an embodiment of the present disclosure. In the example described below, the occurrence of altitude illness is predicted on the basis of only the change of the pulse for ease of description; but the prediction of the occurrence of altitude illness in this example may be performed on the basis of both of the pulse and the blood oxygen content.

With reference to FIG. 5, first, the biological information change prediction unit 332 acquires, at a certain time point, the information of the pulse, the number of steps, and the altitude of the user from the sensor information acquisition unit 331 (S141). Next, the biological information change prediction unit 332 assesses whether the altitude is more than 1000 m or not (S143). Here, when the altitude is not more than 1000 m, the biological information change prediction unit 332 does not perform the prediction of the occurrence of altitude illness described below, and accordingly the processing of the action assistance information generation unit 333 is not executed, either. On the other hand, when the altitude is more than 1000 m, the prediction of the occurrence of altitude illness like the following is executed.

In this case, the biological information change prediction unit 332 predicts the pulse, the number of steps, and the altitude five minutes later using the model 3421 like the above (S145). Further, the biological information change prediction unit 332 assesses whether the predicted biological information after change satisfies the condition of altitude illness or not (S147). The condition used for this assessment is, as described above, extracted from the accumulation of measurement values of the pulse and the blood oxygen content in the case where the user has actually suffered from altitude illness. In the case where the predicted biological information after change is assessed as satisfying the condition of altitude illness, the action assistance information generation unit 333 outputs an alert (S149). Specific examples of the action assistance information including an alert outputted here are further described in the subsequent part.

(3-4. Examples of Action Assistance Information)

Figure 6B:
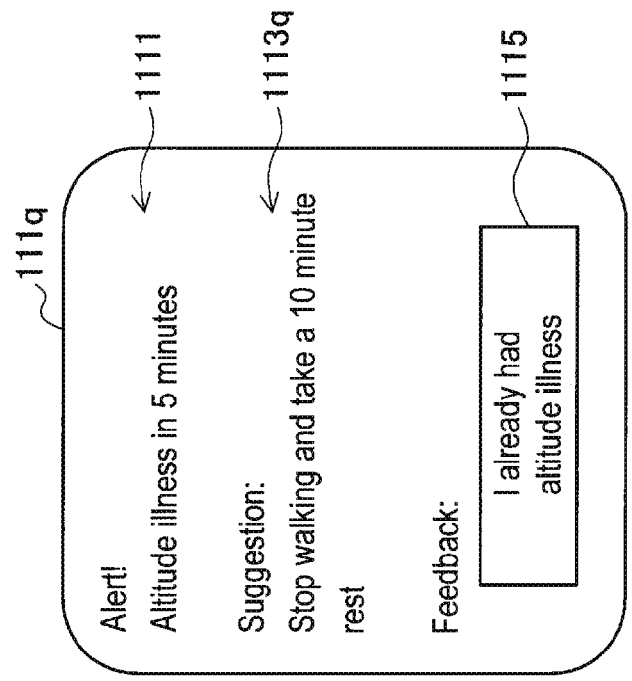
FIGS. 6(A) and 6(B) are diagrams showing a first example of the action assistance information that is provided when the occurrence of altitude illness is predicted in an embodiment of the present disclosure.
Figure 6A:
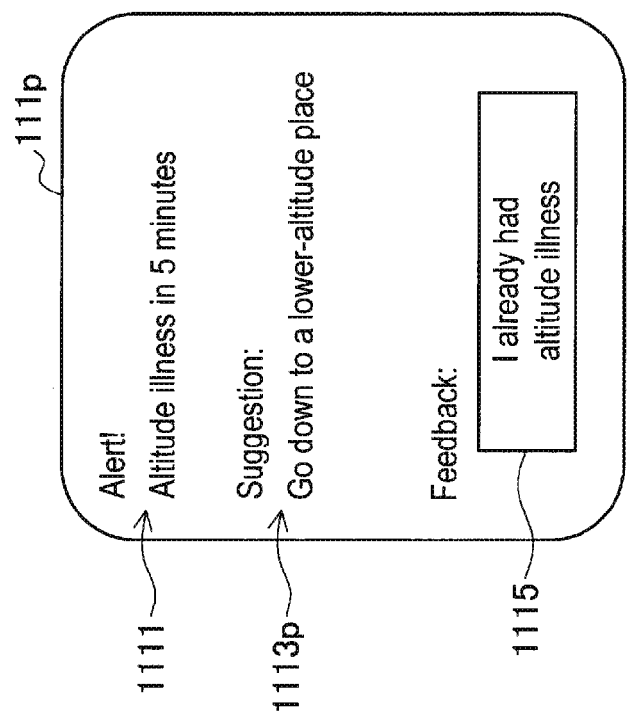

FIGS. 6(A) and 6(B) are diagrams showing a first example of the action assistance information that is provided when the occurrence of altitude illness is predicted in an embodiment of the present disclosure. With reference to FIGS. 6(A) and 6(B), a screen 111 of action assistance information includes an alert 1111, an action proposal 1113, and a feedback button 1115. The screen 111 may be displayed on the display 110 of the terminal apparatus 100, more specifically, the display 110a of the piece of wristwear 100a or the display 110b of the smartphone 100b shown in FIG. 1.

In the illustrated example, one of a screen 111p shown in (A) and a screen 111q shown in (B) is selectively provided. In the screen 111p, an action proposal 1113p proposes going down to a lower-altitude place. On the other hand, in the screen 111q, an action proposal 1113q proposes stopping walking and taking a 10 minute rest.

Such selective provision of action assistance information is enabled by, when a plurality of factors in the change of the biological information are specified by the framework 3422, specifying factors with a large contribution to the change of the biological information, for example. More specifically, in this example, the framework 3422 specifies the number of steps and the altitude as factors in the change of the pulse and the blood oxygen content. The contribution by each factor to the change of the biological information can be estimated from the parameters of the model 3421, more specifically, the components $w_{PS1}$, $w_{PS2}$, $w_{PH1}$, and $w_{PH2}$ of the parameter vector $W_P$ shown in Formula 2 and the components $w_{OS1}$, $w_{OS2}$, $w_{OH1}$, and $w_{OH2}$ of the parameter vector $W_O$ shown in Formula 3. For example, in the case where $(w_{PS1}-w_{PH1})-a(w_{OS1}-w_{OH1})>0$, it is estimated that the number of steps contributes more largely. "a" is a constant determined on the basis of the proportion between the average magnitudes of contribution of the number of steps and the altitude.

The feedback button 1115 is pushed down when the user to whom the action assistance information shown by the screen 111 is presented is already conscious of suffering from altitude illness. In other words, in the illustrated example, the action assistance information includes information that suggests feedback of whether poor physical condition has actually occurred or not. When the user pushes down the feedback button 1115, a label indicating the occurrence of altitude illness is attached to the sensor information that is transmitted from the terminal apparatus 100 to the server 300. Thereby, in the server 300, the accumulation of measurement values in the case where the user has actually suffered from altitude illness can be added.

Figure 7:
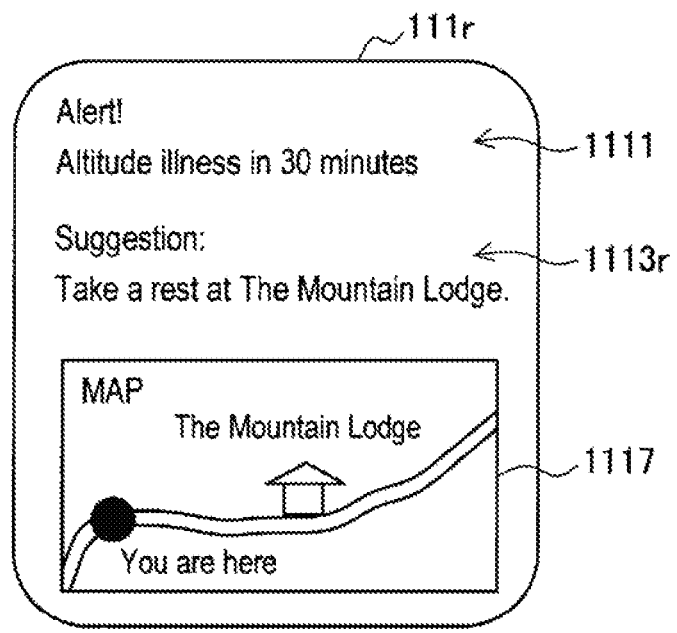
FIG. 7 is a diagram showing a second example of the action assistance information that is provided when the occurrence of altitude illness is predicted in an embodiment of the present disclosure.

FIG. 7 is a diagram showing a second example of the action assistance information that is provided when the occurrence of altitude illness is predicted in an embodiment of the present disclosure. With reference to FIG. 7, a screen 111r of action assistance information includes the alert 1111, an action proposal 1113r, and map information 1117. Similarly to the screen 111 mentioned above, the screen 111r may be displayed on the display 110 of the terminal apparatus 100, more specifically, the display 110a of the piece of wristwear 100a or the display 110b of the smartphone 100b shown in FIG. 1.

In the screen 111r of the illustrated example, the action proposal 1113r proposes taking a rest at a mountain lodge. The map information 1117 shows the location of the user and the location of the mountain lodge. Such action assistance information may be provided in the case where the sensor information provided from the terminal apparatus 100 to the server 300 includes the location information of the user, for example. In this case, the action assistance information generation unit 333 of the server 300 acquires the location information of the user from the sensor information acquisition unit 331, and searches for a facility that is near the user's present location and is useful to avoid poor physical condition (in this example, altitude illness).

By the example described above, the occurrence of altitude illness, which is a type of poor physical condition caused by irregular changes in the condition of the user, can be predicted on the basis of the sensor information. When poor physical condition can be predicted in advance and action assistance information, such as for avoiding poor physical condition, can be provided, the user does not feel an uncomfortable feeling due to poor physical condition or the like and can take action while still having surplus power; thus, this is very useful.

4. MODIFICATION EXAMPLES

The embodiment of the present disclosure is not limited to the examples described above. In the following, some modification examples are described. The embodiment is not limited to those described below, and still more modification examples are possible to the extent that a person skilled in the art can arrive at them naturally.

Figure 8:
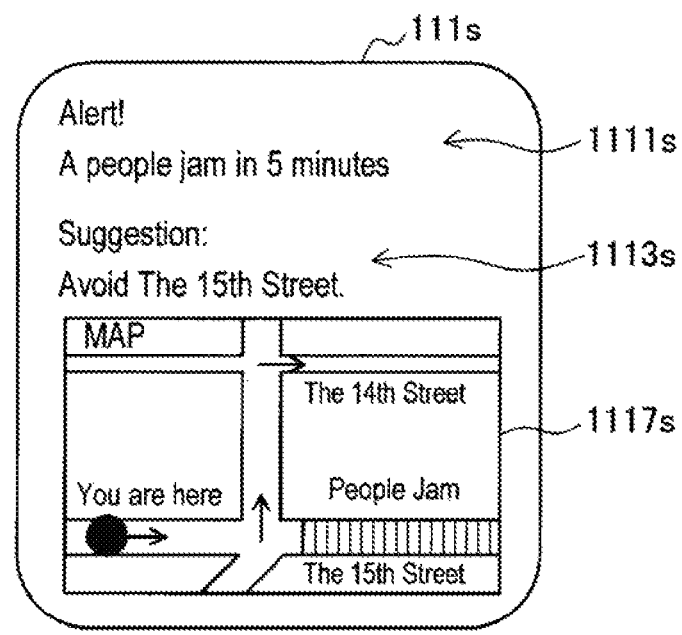
FIG. 8 is a diagram showing an example of the action assistance information that is provided in a modification example of the one embodiment of the present disclosure.

FIG. 8 is a diagram showing an example of the action assistance information that is provided in a modification example of the one embodiment of the present disclosure. With reference to FIG. 8, a screen 111s of action assistance information includes an alert 1111s, an action proposal 1113s, and map information 1117s. Similarly to the screen 111 mentioned above, the screen 111s may be displayed on the display 110 of the terminal apparatus 100, more specifically, the display 110a of the piece of wristwear 100a or the display 110b of the smartphone 100b shown in FIG. 1.

In the screen 111s, the alert 1111s warns that the user would enter a people jam in five minutes if the user continues to walk. In view of this, the action proposal 1113s proposes avoiding "15th Street," and the map information 1117s presents a route to avoid "15h Street." In this example, avoiding a predicted people jam in front is proposed to a user who feels ill when placed in a people jam.

It is known that there are users who are likely to feel ill in a people jam, but this feeling is not necessarily common poor physical condition like altitude illness. However, in this modification example, a framework 3422 for such poor physical condition can be formed by, when the fact that the user suffers from poor physical condition is detected by input information or sensor information, analyzing the biological information at that time or the tendency of other sensor information.

For example, in this modification example, the sensor information acquisition unit 331 of the server 300 acquires sensor information including the pulse of the user, the sound around the user, and location information. Here, when, for example, the correlation between the fact that the pulse of the user is well more than the average value and the fact that noise due to a people jam is detected around the user is high, the user is specified as a user having a tendency to feel ill in a people jam. The framework 3422 configured on the basis of such an analysis specifies noise due to a people jam appearing around the user as a factor in the change of the pulse of the user, for example. Further, the framework 3422 defines predicting the occurrence of noise due to a people jam on the basis of the prediction of turnout in the relevant period of time (this information is separately given as set information, for example) in the user's destination (estimated on the basis of the history of the location information of the user). In accordance with the framework 3422 like the above, the biological information change prediction unit 332 can predict whether, for example five minutes later, the pulse of the user increases to a level at which the user feels ill due to the user's entering a people jam or not.

Thus, the modification example of the embodiment of the present disclosure includes an example in which, even for poor physical condition that is not necessarily common, the framework 3422 is created by, for example, accumulating and analyzing the history of the sensor information of the user, and a change of the biological information that leads to such poor physical condition can be predicted in accordance with the framework 3422.

Further, in the above example shown in FIG. 2, the processor forming the processing unit 330 of the server 300 operates in accordance with a program stored in a memory or a storage, and thereby the functions of the sensor information acquisition unit 331, the biological information change prediction unit 332, the action assistance information generation unit 333, and the model construction unit 334 are implemented; but the embodiment of the present disclosure is not limited such an example. For example, the function of the action assistance information generation unit 333 may be implemented by an external device other than the server 300. In this case, the server 300 transmits information showing the predicted change of the biological information of the user to the external device. Also the function of the model construction unit 334 may be implemented by an external device other than the server 300. In this case, the server 300 imports the prediction rule 342 (including the model 3421) for predicting the change of the biological information of the user from the external device via the network 200, a removable medium, or the like.

Further, the components of the system according to the embodiment of the present disclosure are not limited to the example of the system 10 shown in FIG. 1 in the above. For example, in another embodiment, the system may be complete in a single device, for example in a mobile terminal, a wearable terminal, or the like. In other words, the functional configuration of the sensor information acquisition unit 331 and the biological information change prediction unit 332 described in the above etc. may be provided not in a server but in a terminal apparatus.

5. HARDWARE CONFIGURATION

Next, with reference to FIG. 9, a hardware configuration of an information processing apparatus according to the embodiment of the present disclosure is explained. FIG. 9 is a block diagram illustrating a hardware configuration example of the information processing apparatus according to the embodiment of the present disclosure. The illustrated information processing device 900 may realize a device such as the terminal apparatus the foregoing embodiments, for example.

The information processing apparatus 900 includes a central processing unit (CPU) 901, read only memory (ROM) 903, and random access memory (RAM) 905. In addition, the information processing apparatus 900 may include a host bus 907, a bridge 909, an external bus 911, an interface 913, an input apparatus 915, an output apparatus 917, a storage apparatus 919, a drive 921, a connection port 923, and a communication apparatus 925. Moreover, the information processing apparatus 900 may include an imaging apparatus 933, and a sensor 935, as necessary. The information processing apparatus 900 may include a processing circuit such as a digital signal processor (DSP), an application-specific integrated circuit (ASIC), or a field-programmable gate array (FPGA), alternatively or in addition to the CPU 901.

The CPU 901 serves as an arithmetic processing apparatus and a control apparatus, and controls the overall operation or a part of the operation of the information processing apparatus 900 in accordance with various programs recorded in the ROM 903, the RAM 905, the storage apparatus 919, or a removable recording medium 927. The ROM 903 stores programs, operation parameters, and the like used by the CPU 901. The RAM 905 transiently stores programs used when the CPU 901 is executed, and various parameters that change as appropriate when executing such programs. The CPU 901, the ROM 903, and the RAM 905 are connected with each other via the host bus 907 configured from an internal bus such as a CPU bus or the like. In addition, the host bus 907 is connected to the external bus 911 such as a Peripheral Component Interconnect/Interface (PCI) bus via the bridge 909.

The input apparatus 915 is a device operated by a user such as a mouse, a keyboard, a touch panel, a button, a switch, and a lever. The input apparatus 915 may be a remote control device that uses, for example, infrared radiation and another type of radiowave. Alternatively, the input apparatus 915 may be an external connection apparatus 929 such as a mobile phone that corresponds to an operation of the information processing apparatus 900. The input apparatus 915 includes an input control circuit that generates input signals on the basis of information which is input by the user to output the generated input signals to the CPU 901. The user inputs various types of data to the information processing apparatus 900 and instructs the information processing apparatus 900 to perform a processing operation by operating the input apparatus 915.

The output apparatus 917 includes an apparatus that can report acquired information to the user visually, audibly, or haptically. The output apparatus 917 may be, for example, a display device such as a liquid crystal display (LCD) or an organic electro-luminescence (EL) display, an audio output apparatus such as a speaker or a headphone, or a vibrator. The output apparatus 917 outputs a result obtained through a process performed by the information processing apparatus 900, in the form of video such as text and an image, sounds such as voice and audio sounds, or vibration.

The storage apparatus 919 is an apparatus for data storage that is an example of a storage unit of the information processing apparatus 900. The storage apparatus 919 includes, for example, a magnetic storage device such as a hard disk drive (HDD), a semiconductor storage device, an optical storage device, or a magneto-optical storage device. The storage apparatus 919 stores therein the programs and various data executed by the CPU 901, various data acquired from an outside, and the like.

The drive 921 is a reader/writer for the removable recording medium 927 such as a magnetic disk, an optical disc, a magneto-optical disk, and a semiconductor memory, and built in or externally attached to the information processing apparatus 900. The drive 921 reads out information recorded on the mounted removable recording medium 927, and outputs the information to the RAM 905. The drive 921 writes the record into the mounted removable recording medium 927.

The connection port 923 is a port used to connect devices to the information processing apparatus 900. The connection port 923 may include, for example, a Universal Serial Bus (USB) port, an IEEE1394 port, and a Small Computer System Interface (SCSI) port. The connection port 923 may further include an RS-232C port, an optical audio terminal, a High-Definition Multimedia Interface (HDMI) (registered trademark) port, and so on. The connection of the external connection device 929 to the connection port 923 makes it possible to exchange various data between the information processing apparatus 900 and the external connection device 929.

The communication apparatus 925 is a communication interface including, for example, a communication device for connection to a communication network 931. The communication apparatus 925 may be, for example, a communication card for a local area network (LAN), Bluetooth (registered trademark), Wi-Fi, or a wireless USB (WUSB). The communication apparatus 925 may also be, for example, a router for optical communication, a router for asymmetric digital subscriber line (ADSL), or a modem for various types of communication. For example, the communication apparatus 925 transmits and receives signals in the Internet or transmits signals to and receives signals from another communication device by using a predetermined protocol such as TCP/IP. The communication network 931 to which the communication apparatus 925 connects is a network established through wired or wireless connection. The communication network 931 may include, for example, the Internet, a home LAN, infrared communication, radio communication, or satellite communication.

The imaging apparatus 933 is an apparatus that captures an image of a real space by using an image sensor such as a charge coupled device (CCD) and a complementary metal oxide semiconductor (CMOS), and various members such as a lens for controlling image formation of a subject image onto the image sensor, and generates the captured image. The imaging apparatus 933 may capture a still image or a moving image.

The sensor 935 is various sensors such as an acceleration sensor, an angular velocity sensor, a geomagnetic sensor, an illuminance sensor, a temperature sensor, a barometric sensor, and a sound sensor (microphone). The sensor 935 acquires information regarding a state of the information processing apparatus 900 such as a posture of a housing of the information processing apparatus 900, and information regarding an environment surrounding the information processing apparatus 900 such as luminous intensity and noise around the information processing apparatus 900. The sensor 935 may include a global positioning system (GPS) receiver that receives GPS signals to measure latitude, longitude, and altitude of the apparatus.

The example of the hardware configuration of the information processing apparatus 900 has been described. Each of the structural elements described above may be configured by using a general purpose component or may be configured by hardware specialized for the function of each of the structural elements. The configuration may be changed as necessary in accordance with the state of the art at the time of working of the present disclosure.

6. SUPPLEMENT

The embodiments of the present disclosure may include, for example, the above-described information processing apparatus (terminal apparatus or server), the above-described system, the information processing method executed by the information processing apparatus or the system, a program for causing the information processing apparatus to exhibits its function, and a non-transitory physical medium having the program stored therein.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An information processing apparatus including:

a sensor information acquisition unit configured to acquire sensor information including at least biological information of a user; and a biological information change prediction unit configured to predict a change of the biological information from the sensor information in accordance with a framework based on knowledge concerning poor physical condition of the user.

(2)

The information processing apparatus according to (1), wherein the framework specifies information other than the biological information included in the sensor information, as a factor in the change of the biological information.

(3)

The information processing apparatus according to (2), wherein the framework specifies physical information showing a physical behavior of the user, as the factor.

(4)

The information processing apparatus according to (3), wherein the physical information includes information of an acceleration or an angular velocity of the user, and the framework specifies a walking state of the user estimated on a basis of the acceleration or the angular velocity, as the factor.

(5)

The information processing apparatus according to any one of (2) to (4), wherein the framework specifies information of an environment around the user as the factor.

(6)

The information processing apparatus according to (5), wherein the environmental information includes information of an atmospheric pressure around the user, and the framework specifies an altitude of the user estimated on a basis of the atmospheric pressure, as the factor.

(7)

The information processing apparatus according to any one of (1) to (6), wherein the biological information change prediction unit further predicts occurrence of the poor physical condition on a basis of the change of the biological information.

(8)

The information processing apparatus according to any one of (7), further including an action assistance information generation unit configured to generate action assistance information for the user to avoid the poor physical condition when the occurrence of the poor physical condition is predicted.

(9)

The information processing apparatus according to (8), wherein the action assistance information generation unit generates the action assistance information on a basis of location information of the user.

(10)

The information processing apparatus according to (8) or (9), wherein the framework specifies a plurality of factors in the change of the biological information, and the action assistance information includes information that suggests an action that influences a factor with a larger contribution to the change of the biological information among the plurality of factors.

(11)
The information processing apparatus according to any one of (8) to (10),
wherein the action assistance information includes information that suggests feedback of whether the poor physical condition has actually occurred or not.

(12)
An information processing method including:
acquiring sensor information including at least biological information of a user; and
predicting a change of the biological information from the sensor information in accordance with a framework based on knowledge concerning poor physical condition of the user.

(13)
A program for causing a computer to execute:
a function of acquiring sensor information including at least biological information of a user; and
a function of predicting a change of the biological information from the sensor information in accordance with a framework based on knowledge concerning poor physical condition of the user.

REFERENCE SIGNS LIST 10 system
100 terminal apparatus
110 display
300 server
310 reception unit
320 transmission unit
330 processing unit
331 sensor information acquisition unit
332 biological information change prediction unit
333 action assistance information generation unit
334 model construction unit

The invention claimed is:

1. An information processing apparatus, comprising:
a central processing unit (CPU) configured to:
acquire, from a plurality of sensors, sensor information including biological information of a user, environmental information of an environment around the user, and location information of the user;
acquire a history of the sensor information, wherein the history of the sensor information comprises first past sensor information and second past sensor information previously acquired by at least one sensor of the plurality of sensors;
generate first information based on the biological information, the environmental information of the environment around the user, and the first past sensor information;
generate a model based on a plurality of factors specified by a framework, wherein
the plurality of factors is specified based on the first information, the history of the sensor information, and one of experiential knowledge associated with a type of a poor physical condition of the user or pathological knowledge associated with the type of the poor physical condition of the user, and
the framework is based on information associated with the poor physical condition of the user;
predict a change of the biological information based on the model and the second past sensor information, wherein the second past sensor information indicates a past occurrence of the poor physical condition of the user,
the change of the biological information of the user from a first time instant to a second time instant is predicted, and
a duration between the first time instant and the second time instant is based on a time duration necessary for the user to take an action to avoid the poor physical condition when the poor physical condition is predicted;
output an alert on a terminal apparatus based on the predicted change of the biological information, wherein the predicted change of the biological information corresponds to the poor physical condition of the user;
generate action assistance information based on the predicted change of the biological information and the location information of the user, wherein
the action assistance information recommends the action to the user in advance to an occurrence of the poor physical condition of the user, and
the action to the user is recommended to avoid the poor physical condition of the user; and
control the terminal apparatus to display the generated action assistance information, wherein
the displayed action assistance information includes an action proposal and a location of a specific place near to the user,
the action proposal is associated with the recommended action and the specific place, and
the specific place is useful to avoid the poor physical condition of the user.

2. The information processing apparatus according to claim 1, wherein the framework specifies information, other than the biological information included in the sensor information, as a first factor of the plurality of factors in the change of the biological information of the user.

3. The information processing apparatus according to claim 2, wherein the framework specifies physical information associated with a user physical behavior as a second factor of the plurality of factors.

4. The information processing apparatus according to claim 3, wherein
the physical information includes at least one of user acceleration information or user angular velocity information,
the framework specifies a user walking state as a third factor of the plurality of factors, and
the CPU is further configured to estimate the user walking state based on the at least one of the user acceleration information or the user angular velocity information.

5. The information processing apparatus according to claim 2, wherein the framework specifies the environmental information as a second factor of the plurality of factors.

6. The information processing apparatus according to claim 5, wherein
the environmental information includes pressure information of atmospheric pressure around the user,
the framework specifies a user altitude as a third factor of the plurality of factors, and
the CPU is further configured to estimate the user altitude based on the pressure information.

7. The information processing apparatus according to claim 1, wherein the CPU is further configured to predict the occurrence of the poor physical condition based on the change of the biological information of the user.

8. The information processing apparatus according to claim 1, wherein
- the action assistance information includes information associated with a factor of the plurality of factors based on a contribution of the factor to the change of the biological information of the user, and
- the contribution of the factor is largest among contributions of the plurality of factors.

9. An information processing method, comprising:
in an information processing apparatus:
- acquiring, by a central processing unit (CPU), sensor information from a plurality of sensors, wherein the sensor information includes biological information of a user, environmental information of an environment around the user, and location information of the user;
- acquiring, by the CPU, a history of the sensor information, wherein the history of the sensor information comprises first past sensor information and second past sensor information previously acquired by at least one sensor of the plurality of sensors;
- generating, by the CPU, first information based on the biological information, the environmental information of the environment around the user, and the first past sensor information;
- generating, by the CPU, a model based on a plurality of factors specified by a framework, wherein
  - the plurality of factors is specified based on the first information, the history of the sensor information, and one of experiential knowledge associated with a type of a poor physical condition of the user or pathological knowledge associated with the type of the poor physical condition of the user, and
  - the framework is based on information associated with the poor physical condition of the user;
- predicting, by the CPU, a change of the biological information based on the model and the second past sensor information, wherein
  - the second past sensor information indicates a past occurrence of the poor physical condition of the user,
  - the change of the biological information of the user from a first time instant to a second time instant is predicted, and
  - a duration between the first time instant and the second time instant is based on a time duration necessary for the user to take an action to avoid the poor physical condition when the poor physical condition is predicted;
- outputting, by the CPU, an alert on a terminal apparatus based on the predicted change of the biological information, wherein the predicted change of the biological information corresponds to the poor physical condition of the user;
- generating, by the CPU, action assistance information based on the predicted change of the biological information and the location information of the user, wherein
  - the action assistance information recommends the action to the user in advance to an occurrence of the poor physical condition of the user, and
  - the action to the user is recommended to avoid the poor physical condition of the user; and
- controlling, by the CPU, the terminal apparatus to display the generated action assistance information, wherein
  - the displayed action assistance information includes an action proposal and a location of a specific place near to the user,
  - the action proposal is associated with the recommended action and the specific place, and
  - the specific place is useful to avoid the poor physical condition of the user.

10. A non-transitory computer-readable medium having stored thereon, computer-executable instructions, which when executed by a computer, cause the computer to execute operations, the operations comprising:
- acquiring, from a plurality of sensors, sensor information including biological information of a user, environmental information of an environment around the user, and location information of the user;
- acquiring a history of the sensor information, wherein the history of the sensor information comprises first past sensor information and second past sensor information previously acquired by at least one sensor of the plurality of sensors;
- generating first information based on the biological information, the environmental information of the environment around the user, and the first past sensor information;
- generating a model based on a plurality of factors specified by a framework, wherein
  - the plurality of factors is specified based on the first information, the history of the sensor information, and one of experiential knowledge associated with a type of a poor physical condition of the user or pathological knowledge associated with the type of the poor physical condition of the user, and
  - the framework is based on information associated with the poor physical condition of the user;
- predicting a change of the biological information based on the model and the second past sensor information, wherein
  - the second past sensor information indicates a past occurrence of the poor physical condition of the user,
  - the change of the biological information of the user from a first time instant to a second time instant is predicted, and
  - a duration between the first time instant and the second time instant is based on a time duration necessary for the user to take an action to avoid the poor physical condition when the poor physical condition is predicted;
- outputting an alert on a terminal apparatus based on the predicted change of the biological information, wherein the predicted change of the biological information corresponds to the poor physical condition of the user;
- generating action assistance information based on the predicted change of the biological information and the location information of the user, wherein
  - the action assistance information recommends the action to the user in advance to an occurrence of the poor physical condition of the user, and
  - the action to the user is recommended to avoid the poor physical condition of the user; and
- controlling the terminal apparatus to display the generated action assistance information, wherein
  - the displayed action assistance information includes an action proposal and a location of a specific place near to the user,
  - the action proposal is associated with the recommended action and the specific place, and
  - the specific place is useful to avoid the poor physical condition of the user.

* * * * *